(12) United States Patent
Martin et al.

(10) Patent No.: US 10,307,560 B2
(45) Date of Patent: Jun. 4, 2019

(54) POSITIVE AIRWAY PRESSURE DEVICE

(71) Applicant: ResMed Limited, Bella Vista, New South Wales (AU)

(72) Inventors: Dion Charles Chewe Martin, Sydney (AU); Barton John Kenyon, Sydney (AU); Alexander Virr, Gosford (AU); Dmitri Anatolievich Doudkine, Sydney (AU); Philip Rodney Kwok, Sydney (AU); Richard Charles Napper, Sydney (AU); John Michael Snow, Sydney (AU)

(73) Assignee: ResMed Limited, Bella Vista (AU)

( * ) Notice: Subject to any disclaimer, the term of this patent is extended or adjusted under 35 U.S.C. 154(b) by 907 days.

(21) Appl. No.: 14/663,908

(22) Filed: Mar. 20, 2015

(65) Prior Publication Data

US 2015/0190605 A1    Jul. 9, 2015

Related U.S. Application Data

(63) Continuation of application No. 13/896,515, filed on May 17, 2013, now Pat. No. 9,010,324, which is a
(Continued)

(51) Int. Cl.
*A61M 16/00*   (2006.01)
*A61M 16/16*   (2006.01)
(Continued)

(52) U.S. Cl.
CPC ........ *A61M 16/16* (2013.01); *A61M 16/0003* (2014.02); *A61M 16/0066* (2013.01); *A61M 16/0069* (2014.02); *A61M 16/06* (2013.01); *A61M 16/0816* (2013.01); *A61M 16/0875* (2013.01); *A61M 16/108* (2014.02); *A61M 16/109* (2014.02); *A61M 16/1075* (2013.01);
(Continued)

(58) Field of Classification Search
CPC .............. A61M 16/16; A61M 16/0066; A61M 2205/3653; A61M 2205/3666; A61M 2205/42; A61M 2205/502; A61M 2205/6081; A61M 2205/8206; A61M 2205/8262; A61M 16/06; A61M 16/0875; A61M 16/1075; A61M 16/108; A61M 16/003; A61M 16/0069; A61M 16/109; A61M 16/0816; A61M 2016/003; A61M 2205/3334; A61M 2205/3368
See application file for complete search history.

(56) References Cited

U.S. PATENT DOCUMENTS 6,715,739 B2    4/2004   Mulvaney et al.
6,910,483 B2    6/2005   Daly et al.
(Continued)

*Primary Examiner* — Steven O Douglas
(74) *Attorney, Agent, or Firm* — Nixon & Vanderhye P.C.

(57) ABSTRACT

A positive airway pressure (PAP) device for supplying a flow of breathable gas to a patient includes a flow generator configured to pressurize a flow of breathable gas and a humidifier configured to receive and humidify the pressurized flow of breathable gas from the flow generator. The PAP device also includes a power source. The flow generator, humidifier and power source are positioned so that heat generated by at least one of the flow generator and the power source is conveyed to water in the humidifier.

21 Claims, 11 Drawing Sheets

Related U.S. Application Data continuation of application No. 12/615,503, filed on Nov. 10, 2009, now Pat. No. 8,453,640.

(60) Provisional application No. 61/113,715, filed on Nov. 12, 2008.

(51) Int. Cl.
*A61M 16/06* (2006.01)
*A61M 16/08* (2006.01)
*A61M 16/10* (2006.01)

(52) U.S. Cl.
CPC ............... *A61M 2016/003* (2013.01); *A61M 2205/3334* (2013.01); *A61M 2205/3368* (2013.01); *A61M 2205/3653* (2013.01); *A61M 2205/3666* (2013.01); *A61M 2205/42* (2013.01); *A61M 2205/502* (2013.01); *A61M 2205/6081* (2013.01); *A61M 2205/8206* (2013.01); *A61M 2205/8262* (2013.01)

(56) References Cited

U.S. PATENT DOCUMENTS

| | | |
|---|---|---|
| 7,096,864 B1 | 8/2006 | Mayer et al. |
| 7,617,823 B2 | 11/2009 | DiMatteo et al. |
| 7,677,246 B2 | 3/2010 | Kepler et al. |
| 7,866,944 B2 | 1/2011 | Kenyon et al. |
| 8,555,879 B2 * | 10/2013 | Potharaju .......... A61M 16/0066 128/203.12 |
| 2008/0072900 A1 | 3/2008 | Kenyon et al. |
| 2008/0105257 A1 | 5/2008 | Klasek et al. |
| 2008/0304986 A1 | 12/2008 | Kenyon et al. |
| 2009/0136341 A1 | 5/2009 | Kenyon |
| 2009/0223514 A1 | 9/2009 | Smith et al. |
| 2009/0246013 A1 | 10/2009 | Kenyon et al. |
| 2010/0065051 A1 | 3/2010 | Potharaju et al. |
| 2010/0132708 A1 | 6/2010 | Martin et al. |
| 2013/0247911 A1 | 9/2013 | Martin et al. |

* cited by examiner

POSITIVE AIRWAY PRESSURE DEVICE

CROSS REFERENCE TO RELATED APPLICATIONS

This application is a continuation of U.S. application Ser. No. 13/896,515, filed May 17, 2013, now allowed, which is a continuation of U.S. application Ser. No. 12/615,503, filed Nov. 10, 2009, now U.S. Pat. No. 8,453,640, which claims priority to U.S. Application 61/113,715, filed Nov. 12, 2008, the entire contents of each are incorporated herein by reference in their entirety.

FIELD OF THE INVENTION

The present invention relates to positive airway pressure devices for respiratory therapy for treating, for example, Sleep Disordered Breathing (SDB). The present invention also relates to components for positive pressure airway devices.

BACKGROUND OF THE INVENTION

Positive Airway Pressure (PAP), including Continuous Positive Airway Pressure (CPAP), is a form of Noninvasive Positive Pressure Ventilation (NIPPV) for the treatment of Osbtructive Sleep Apnea (OSA). PAP treatment involves the delivery of a pressurized breathable gas, usually air, to a patient's airways using a conduit and a patient interface, for example, a mask. Gas pressures employed for CPAP treatment typically range from 4 cm $H_2O$ to 20 cm $H_2O$, at flow rates of up to 180 l/min (measured at the patient interface), depending on patient requirements. The pressurized gas acts as a pneumatic splint for the patient's airway, preventing airway collapse, especially during the inspiratory phase of respiration.

CPAP machines including an airflow generator for supplying pressurized air to the patient are known, and over recent years there has been commercial incentive for more compact CPAP machines. However, in seeking to reduce the size of the CPAP machines there has been a trade-off between reduced size on the one hand and reduced performance on the other.

The advantages of incorporating humidification of the air supply to a patient are known, and CPAP machines are known which incorporate humidifying devices, either separately from the flow generator or integrated therewith. An example of an integrated flow generator/humidifier is the ResMed® S7 sold by the assignee of the present application. An example of a humidifier which is separately provided to be connectable to a flow generator is disclosed in co-pending, commonly assigned U.S. Patent Application Publication 2008/0072900 A1.

It is known to provide a heating unit, such as a heating plate, to a humidifier to increase the amount of water vapor in the flow of breathable gas. Reducing the size of CPAP machines, including humidifiers, has led to a decrease in the size of water containers making it more difficult to provide humidification of the air supply during the entirety of the patient's sleep cycle. The reduction in the size of humidifier tubs results in a decrease in the surface area of the water exposed to the flow of air provided by the flow generator. This creates problems in maintaining a sufficient moisture pickup. The integration of humidifiers with flow generators also makes it more difficult to clean the water container of the humidifier due to complex shapes of the tub and cover.

Humidifiers which are attachable to the flow generator also suffer from certain drawbacks. In some instances, the humidifier increases the size of the footprint of the device, meaning a table or stand may no longer be of suitable size to hold the device once the humidifier is attached. Some humidifiers also have seals that are submerged and that may tend to deteriorate over time with prolonged contact to water, increasing the propensity for leaks.

Some attachable humidifiers include a metal base to transfer heat from the heating plate to the water in the humidifier. The metal in these plates may corrode over time, reducing the effectiveness, even destroying, the humidifier. Additionally, extra electrical contacts need to be attached to the humidifier to provide power to the heating plate, and, since the heating plate is often positioned under the water supply, there is a design requirement to prevent spilled water from reaching electrical components.

The heat in the PAP device itself may often build up and reduce bearing life within the device. PAP devices also generate noise during operation, and this noise must be controlled so that it does not interfere with patient sleep.

SUMMARY OF THE INVENTION

One aspect of the invention relates to a PAP device that comprises components that are configured to be connected to present a reduced footprint.

Another aspect of the invention relates to a PAP device that comprises components that may be exchanged with other components.

A further aspect of the invention relates to a PAP device that comprises a humidifier to provide a flow of humidified air and the humidifier may be one of a plurality of humidifiers of varying size that are all configured to be connected to the PAP device.

A still further aspect of the invention relates to a PAP device that includes a humidifier configured to store a supply of water that is easily accessible.

An even further aspect of the invention relates to a PAP device that improves heat conduction to the flow of air, a supply of water that humidifies the air, and/or the humidified air flow.

Another aspect of the invention relates to a PAP device in which residual heat from a flow generator configured to generate a flow of breathable gas and/or heat from a heating element are conducted to the flow of air, a supply of water that humidifies the air, and/or the humidified air flow.

Still another aspect of the invention relates to a PAP device that reduces the noise produced by operation of the PAP device.

Another aspect of the invention relates to a PAP device that may comprise a humidifier configured to store a supply of water to humidify the flow of air and that has a reduced possibility of leakage.

Yet another aspect of the invention relates to a PAP device that comprises a heating element configured to heat the air flow and/or water to humidify the air flow.

A further aspect of the invention relates to a PAP device that includes a humidifier component that is more easily connected to a flow generator than currently available devices.

A further aspect of the invention relates to a PAP device that includes a power supply and control to supply power and control to a flow generator configured to generate the flow of breathable gas and/or a heating element that is configured to heat the flow of breathable gas and/or a supply of water to humidify the flow in which the power supply and control and/or heating element is at less risk of water leaking into the power supply and control and/or the heating element.

According to a sample embodiment of the invention, a positive airway pressure (PAP) device for supplying a flow of breathable gas to a patient comprises a first housing; a flow generator provided in the first housing, the flow generator configured to generate a flow of breathable gas; a second housing configured to be connected to the first housing, the second housing comprising a channel comprising an inlet configured to receive the flow of breathable gas and an outlet configured to discharge the flow of breathable gas, wherein the first housing is provided on top of the second housing such that a footprint of the PAP device is not substantially increased beyond a footprint of the second housing.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

PAP Device First Embodiment

Figure 1A:
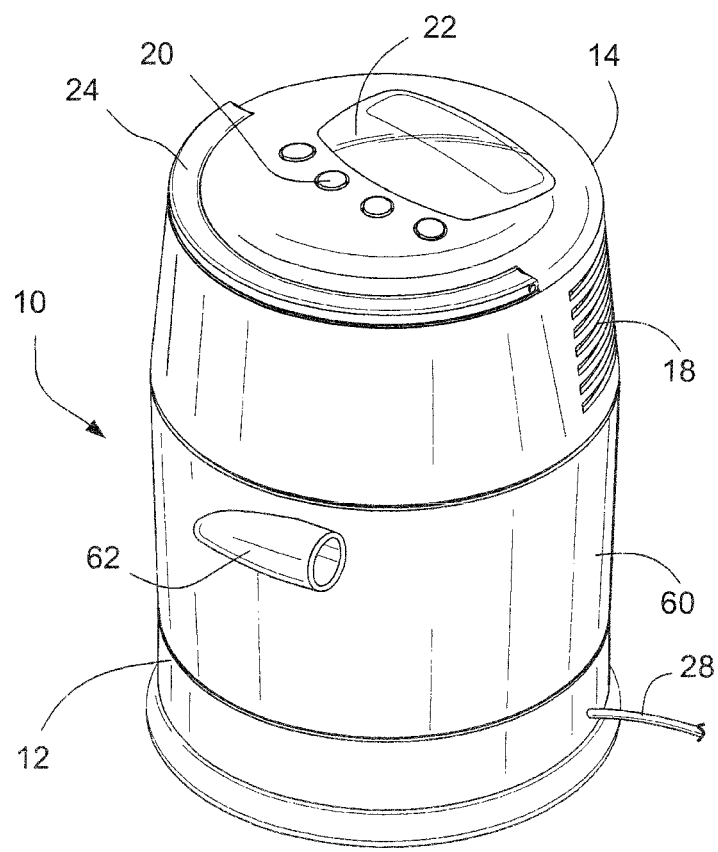
FIG. 1A schematically illustrates a PAP device including a humidifier according to a sample embodiment of the invention.
Figure 1B:
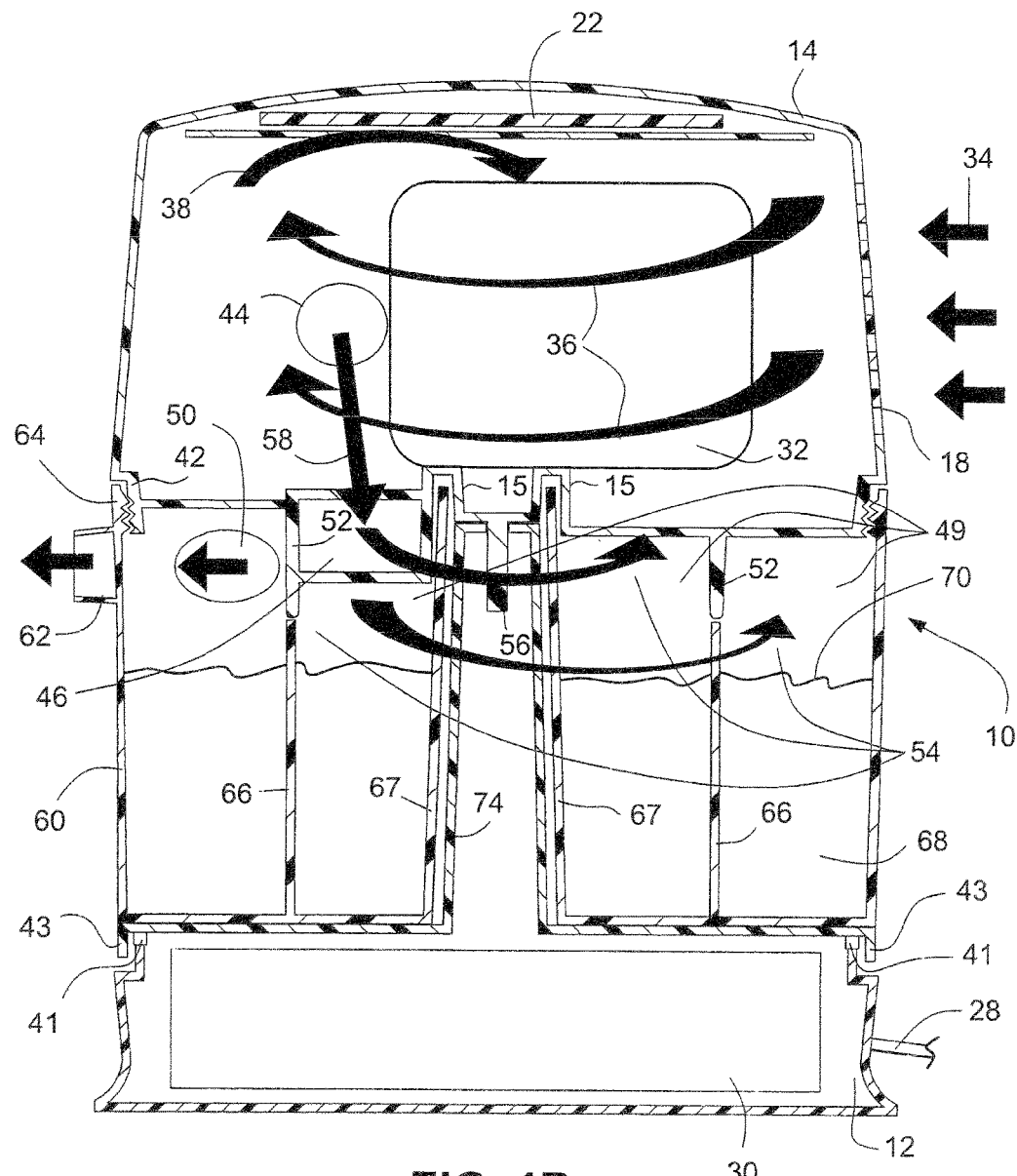
FIG. 1B schematically illustrates a cross section of the PAP device of FIG. 1A.

Referring to FIGS. 1A and 1B, a PAP device 10 according to a sample embodiment may comprise a flow generator provided in a flow generator housing 14 and a humidifier 60 configured to contain a supply of water to humidify the flow of breathable gas generated by the flow generator. The humidifier 60 comprises an outlet 62 that is tangentially provided on the outer surface. The PAP device 10 may be configured to be portable and include a handle 24 provided to the flow generator housing part 14. The PAP device 10 may be sized to be carried around by the handle 24, or in a small container, such as a tote bag.

The PAP device 10 comprises a power base 12 that is configured to house a power supply and control unit 30. The power base 12 may include an electrical connector 28, for example an electrical cord configured to deliver AC current to the power supply and control unit 30 of the PAP device 10. It should be appreciated that the power supply and control unit 30 may also be powered by a battery, for example a rechargeable battery.

The humidifier 60 may include a threaded portion 64 configured to threadably engage a threaded portion 42 of the flow generator housing 14 to connect the humidifier 60 and the flow generator housing 14. It should be appreciated that an alternative connection arrangement, for example a hinge, may be provided to connect the humidifier 60 and the flow generator housing 14. The humidifier 60 may comprise an inner circumferential wall 67 that is configured to be received in recesses 15 provided in the flow generator housing 14 to align the humidifier 60 and the flow generator housing 14.

A blower motor assembly 32 is provided in the flow generator housing 14 and receives power and controls from the power supply and control unit 30. The blower motor assembly 32 may comprise a motor for rotatably driving at least one impeller to generate a flow of air. Such blower motor assemblies are disclosed in, for example, WO 2007/048205 A1 and WO 2007/048206 A1, the entire contents of both being incorporated herein by reference.

Power and control may be supplied to the blower motor assembly 32 from the power supply and control unit 30 by an electrical connection provided between the power supply and control unit 30 and the blower motor assembly 32 by, for example, an electrical and control connector 56 at the connection between the power base 12 and the flow generator housing 14. The humidifier 60 may also comprise an electrical and control connector 74 configured to receive the electrical and control connector 56 of the flow generator housing 14 and guide the flow generator housing 14 into threaded engagement with the humidifier 60. The connectors 56, 74 may include electrical connections and/or contacts to electrically connect the power supply and control unit 30 to the blower motor assembly 32 and the controls 20. The electrical and control connectors may be circular multipole connectors.

Referring again to FIG. 1A, the flow generator housing 14 of the PAP device 10 may comprise controls 20 and a display 22, for example an LCD. The controls 20 may comprise buttons, although it should be appreciated that other controls, such as knobs or dials, may be provided. The controls 20 may be electrically connected to the power supply and control unit 30 when the power base 12, the humidifier 60, and the flow generator housing 14 are assembled together, for example through the electrical connections and/or contacts 56 described above. The controls 20 may include, for example, an ON/OFF button to turn the blower motor assembly 32 on and off. Other controls may be provided, for example, to set a timer, adjust the speed of the blower motor assembly 32 and/or control a heating plate provided to a humidifier 60, as described in more detail below.

The display 22 may indicate, for example, various operating conditions of the PAP device, including a pressure and/or temperature of the air flow generated by the blower motor assembly 32 and/or a humidity level of the air flow.

The power base 12 may include cooling vents 41 to permit dissipation of heat generated by the power supply and control unit 30. A lip 43 may be provided over the cooling vents 41 to protect the power supply and control unit 30 from accidental spillage. It should also be appreciated that the power base 12 may also be sealed.

The flow generator housing 14 may comprise air inlets 18 formed in a side wall of the flow generator housing 14. When the blower motor assembly 32 is turned on, the blower motor assembly 32 draws inlet air 34 from the ambient through the air inlets 18 of the flow generator housing 14. The inlet air 34 drawn by the blower motor assembly 32 creates an air flow 36 in the flow generator housing 14 that provides an inlet air flow 38 into the blower motor assembly 32.

The inlet air flow 38 is pressurized by the blower motor assembly 32. The amount of pressurization is dependent on, for example, the rotation speed of the impeller(s) of the blower motor assembly 32. The pressurized air flow 58 exits the blower motor assembly 32 into an airway connector 44 provided in the flow generator housing 14 and is then directed by the airway connector 44 into a channel inlet 46. As shown in FIG. 1B, the channel inlet 46 directs the flow into a spiral channel 49 defined by a channel wall 52 provided in the flow generator housing 14. The channel 49 forms the flow into a spiral air flow that is directed to a channel outlet 50 that is provided in fluid communication with the outlet 62 provided on the humidifier 16.

As shown in FIG. 1B, the humidifier 60 may comprise a channel wall 66 that is configured to be generally coplanar with the channel wall 52 of the flow generator housing 14 to define the spiral channel 49 when the humidifier 60 and the flow generator housing 14 are connected. The air flow 58 delivered to the channel inlet 46 by the airway connector 44 is formed into a spiral airflow 54 by the spiral channel 49 formed by the channel walls 52, 66. The air flow 54 passes over the surface 70 of a supply of water 68 provided in the humidifier 60 and the air flow 54 is humidified. As shown in FIG. 3B, the air flow 58 is delivered by the airway connector 44 to the channel inlet 46 generally near the center of the humidifier 60. As the air flow 54 spirals from about the center of the humidifier 60 to the channel outlet 50, the amount of water that the air flow 54 contacts is maximized to improve the humidification of the air flow 54. The humidified air flow 54 is directed by the channel 49 to the channel outlet 50 and exits the humidifier 60 through an outlet 62. A delivery hose or tube may be connected to the outlet 62 to deliver the humidified air flow to a patient interface, for example a mask.

Various factors can affect how much humidity the air flow picks up as it passes through the humidifier 60. These factors may include, but are not limited to, the length of contact with the water, the duration of contact with the water, the temperature of the air flow and/or the water, etc. At least some of these factors may be controlled by a humidification control system contained in the power supply and control unit 30. Such a humidification control system is disclosed in, for example, U.S. Patent Application Publication 2009/0223514 A1, the entire contents of which are incorporated herein by reference. As another example, the length and/or duration of the air flow's contact with the water can be increased by providing baffles in the channel 49 to create a longer path through which the air flows.

Figure 2:
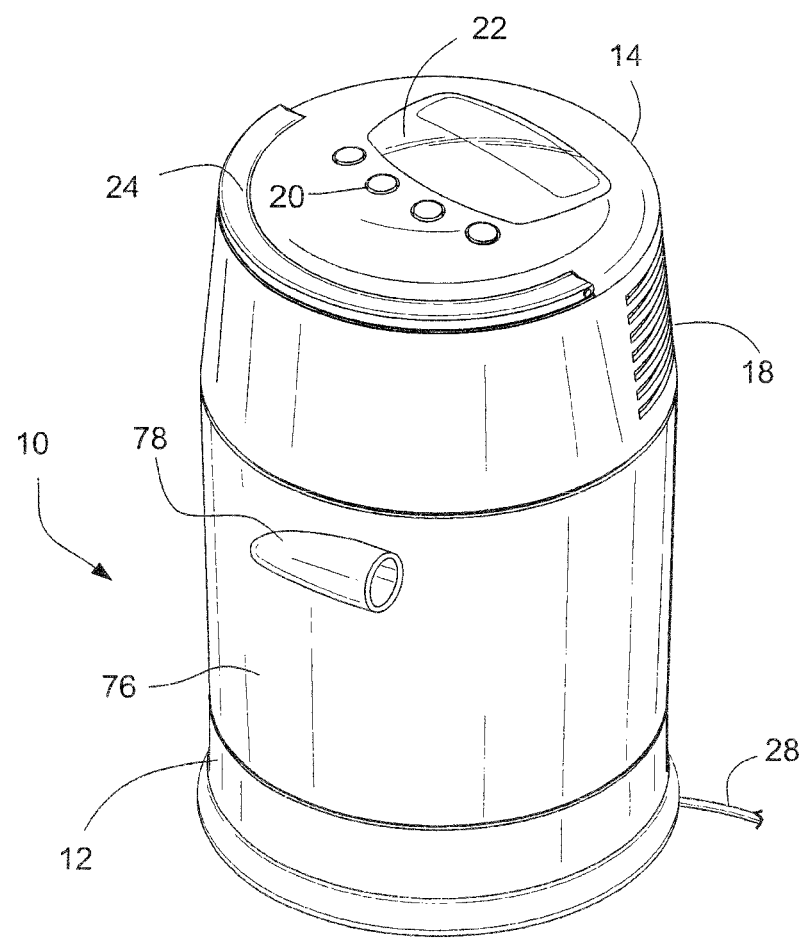
FIG. 2 schematically illustrates a PAP device including a humidifier according to another sample embodiment FIG. 3 schematically illustrates a PAP device according to another sample embodiment.

The humidifier 60 may be configured to contain a supply of water of about 300 ml-800 ml. In a variant shown in FIG. 2, a humidifier 76 having a larger capacity than the humidifier 60 may be provided for connection to the power base 12 and the flow generator housing 14. The humidifier 76 may contain a supply of water of about 500 ml-1600 ml. A delivery hose or tube may be connected to an outlet 78 of the humidifier 76 to deliver a humidified air flow to a patient interface.

PAP Device Second Embodiment

Figure 3:
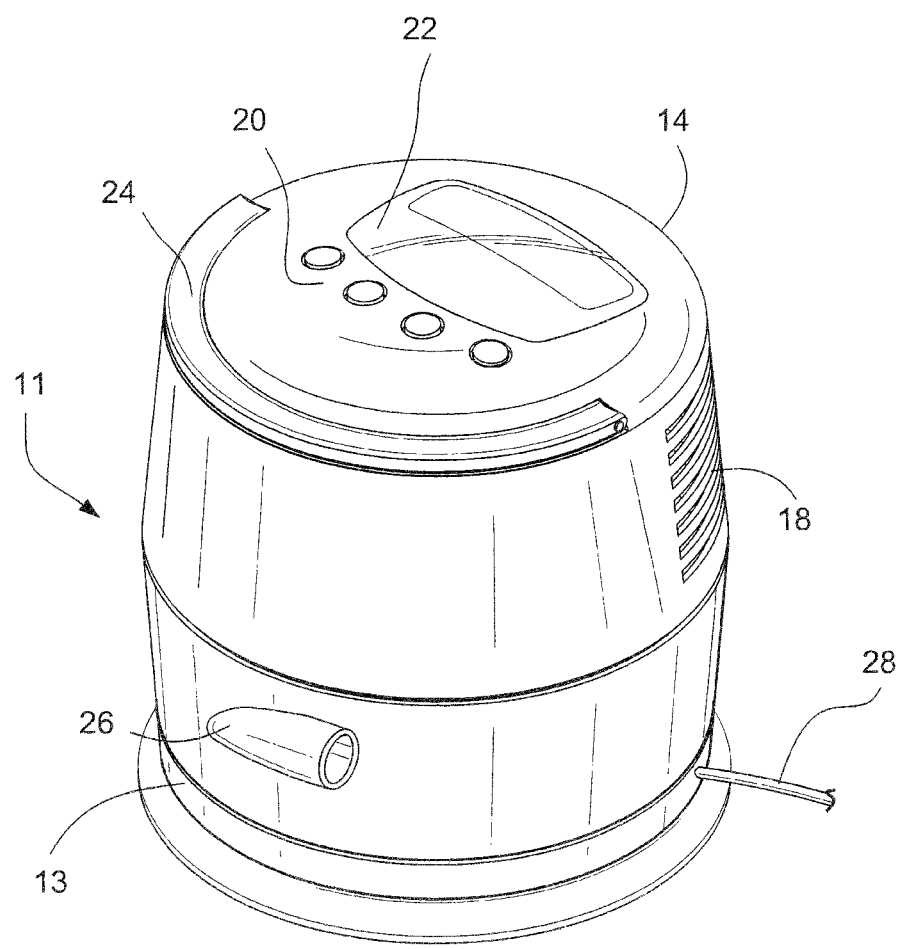
Figure 4A:
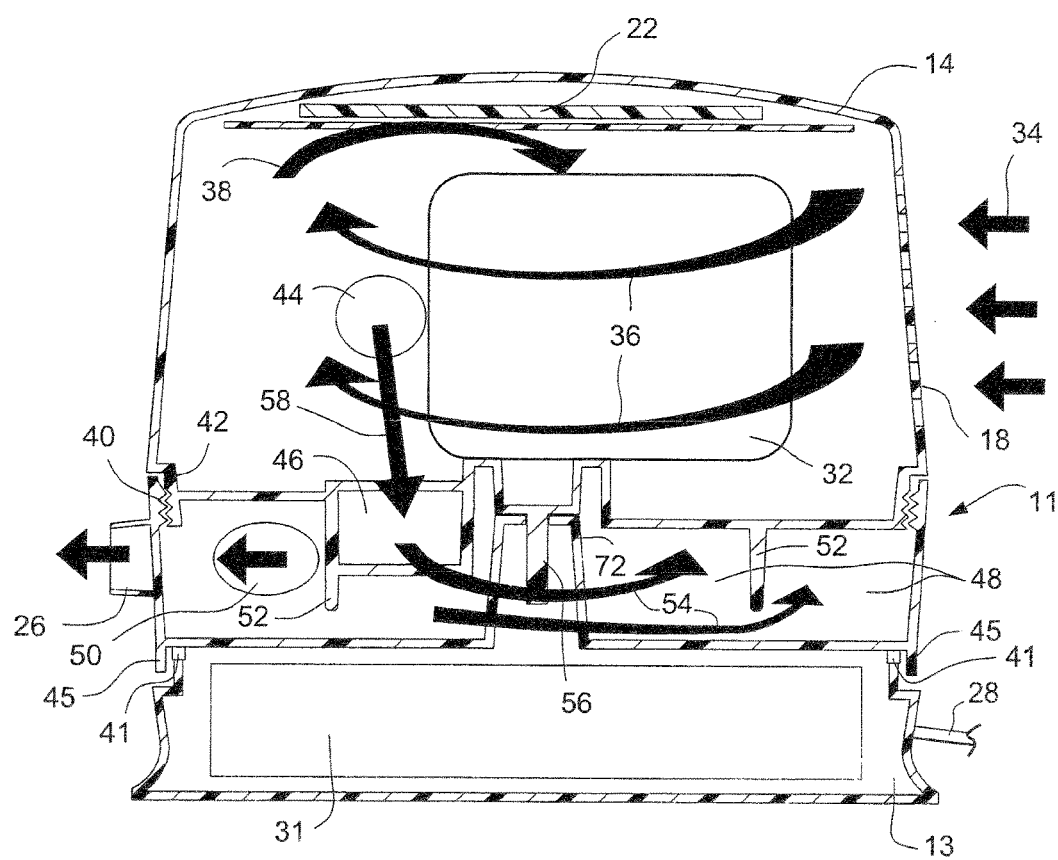
FIG. 4A schematically illustrate a cross section of the PAP device of FIG. 3.
Figure 4B:
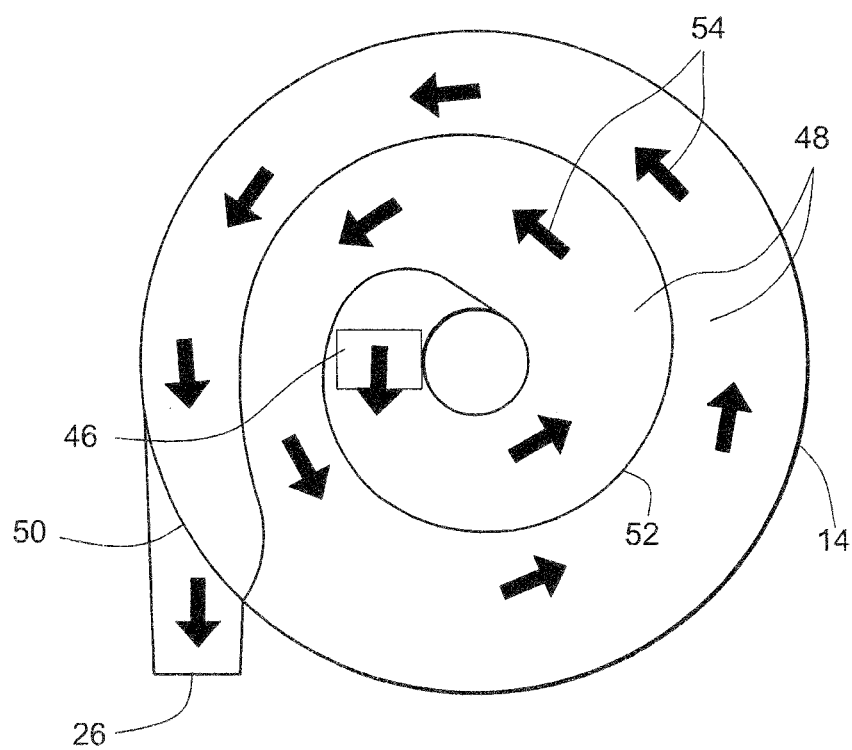
FIG. 4B schematically illustrates an airflow path of the PAP device of FIG. 3.

Referring to FIGS. 3, 4A and 4B, a PAP device 11 according to another sample embodiment of the invention may comprise a power base 13 and the flow generator housing 14. The power base 13 houses a power supply and control unit 31. As shown in FIG. 4A, the flow generator housing 14 includes the threaded portion 42 that is threadably connectable to a threaded portion 40 of the power base 13. It should be appreciated that the flow generator housing 14 and the power base 13 may be connected by other mechanisms, for example a hinge. The flow generator housing 14 may be connected to the power base 13 by the connector 56 and a connector 72. The connectors 56, 72 may be, for example, circular multipole connectors. The power base 13 may include cooling vents 41 that are protected by a lip 45. The power base 13 may be sealed rather than vented.

One or more baffles or mufflers may be provided within the first housing part 14 to reduce the sound of the PAP device 10 during operation. Further, heat from the blower motor assembly 32, and/or an independently operable heater may be used to heat the air as it passes through the PAP device 11, if it is desired to deliver heated air to a patient.

Referring to FIGS. 4A and 4B, the flow generator housing 14 comprises the spiral channel wall 52 that defines a spiral channel 48. It should be appreciated that although the channel is shown as spiral, it should be appreciated that the flow of air could be more direct, or through passageways other than spiral. In the embodiment illustrated, the air flow is directed through the spiral channel 48 to replicate the air flow path of the humidifier described above, where the spiral will minimize resistance to the air flow. Heat generated by the flow generator, i.e. the blower motor assembly 32, may be used to heat the air flow in the channel 48. Further, although not shown in the drawings, it should be appreciated that baffles may be provided within the channel 48 to reduce the sound of the air flow through the device.

Figure 5:
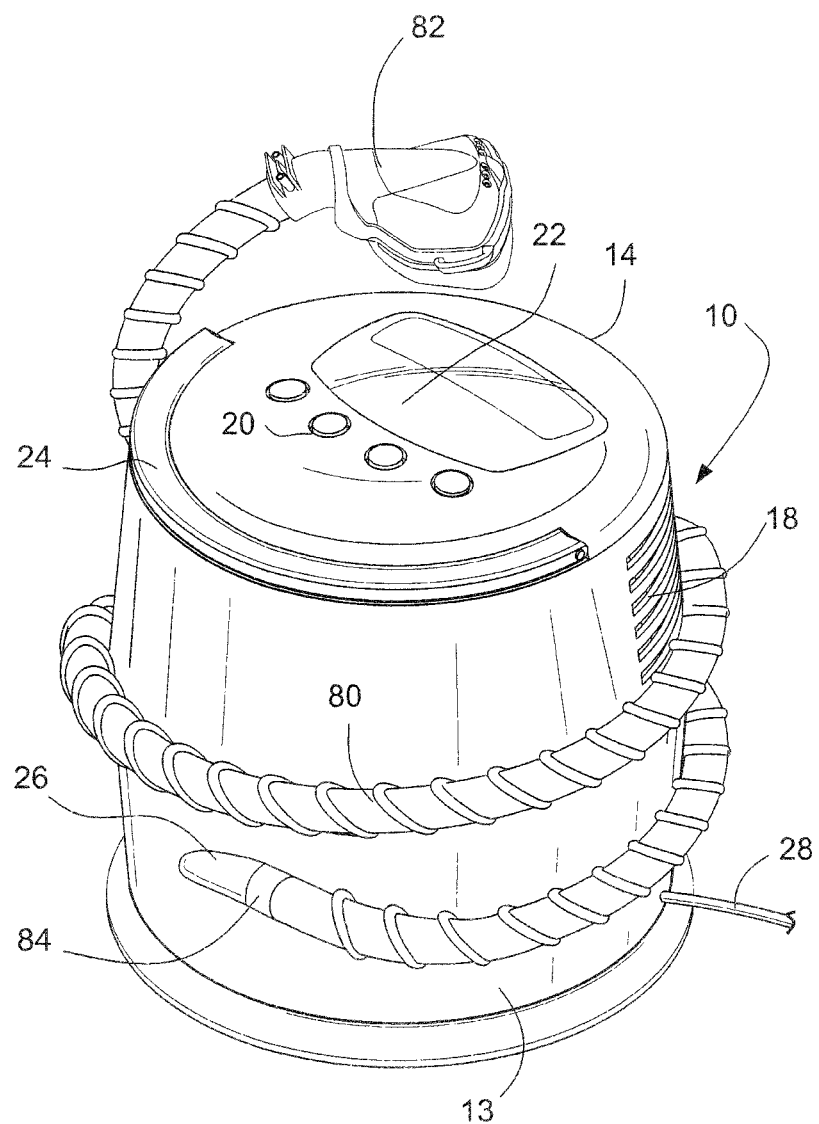
FIG. 5 schematically illustrates a PAP device according to another sample embodiment of the invention.

As shown in FIG. 5, a tube, or hose, 80 may be connected to the outlet 26, for example by a connector 84, to deliver the air flow to a patient interface 82, for example a mask. The hose 80 may be wrapped around the perimeter of the PAP device 11 for storage or shipment of the PAP device 11. The flow generator housing 14 may include a clip, or cleat, or recess for securing the patient interface 82 to the PAP device 10. Although the hose is shown wrapped around the PAP device 11 that does not include a humidifier, it should be appreciated that the hose may be wrapped around the PAP device 10 described above with respect to FIGS. 1A-2 that includes a humidifier.

As shown in FIGS. 1-5, the PAP device 10, 11 has the same footprint regardless of whether the PAP device is provided without a humidifier, a humidifier having a first capacity, or a humidifier having a second, larger capacity. It should be appreciated that various stackable configurations are possible, including placing the flow generator housing 14 below the humidifier 60, 76 or placing the power base 12 and the flow generator housing 14 above the humidifier 60, 76. It should be also be appreciated that the base 12 and the flow generator housing 14 may be combined into one unit and placed above or below the humidifier 60,76. In the event that the flow generator housing 14 is placed below another component, it may be desirable to place the controls and display in a more accessible location, for example on a side of the flow generator housing, or the power base.

PAP Device Third Embodiment

Figure 6:
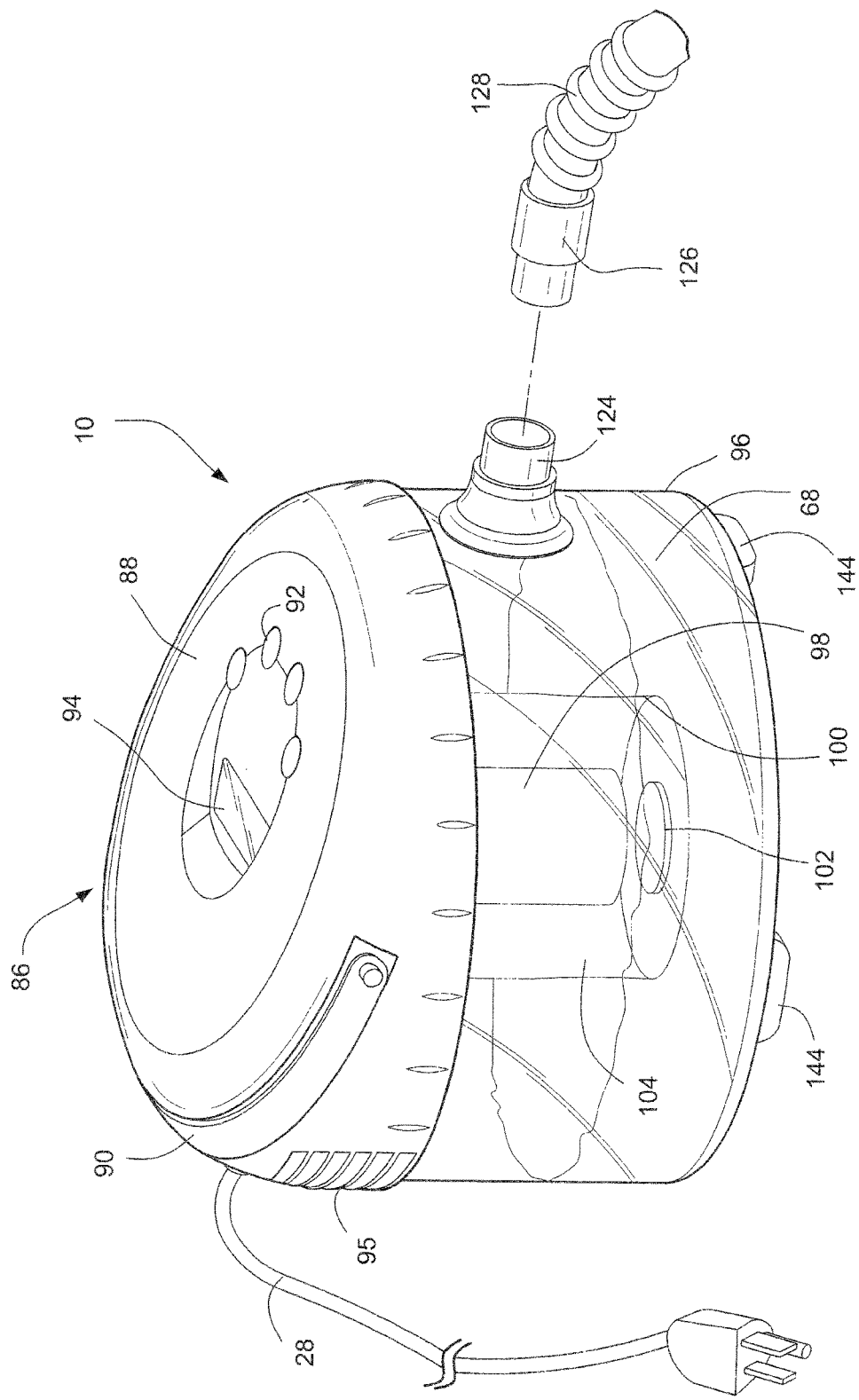
FIG. 6 schematically illustrates a PAP device including a humidifier according to another sample embodiment of the invention.
Figure 7A:
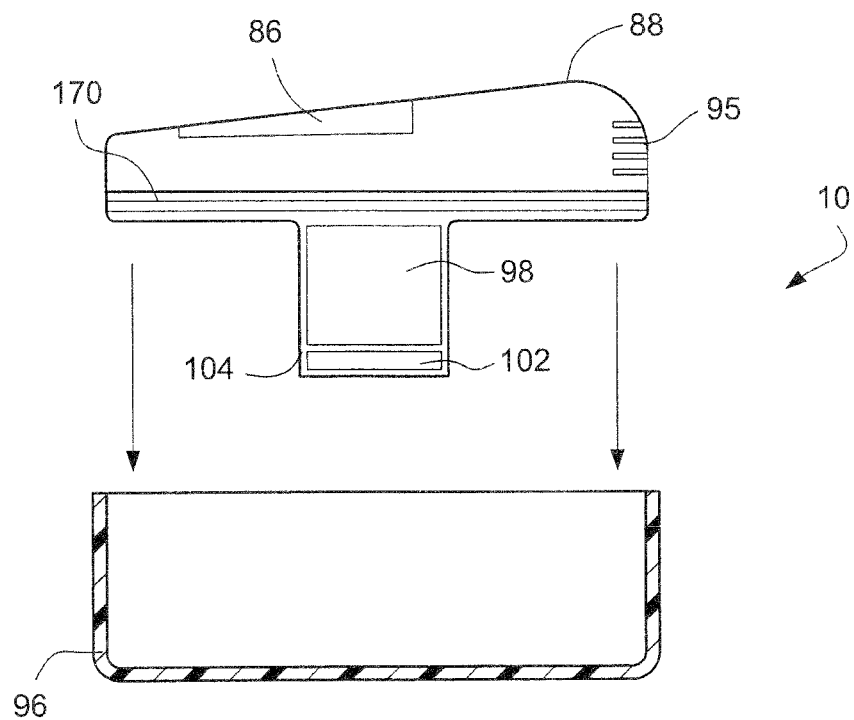
FIGS. 7A and 7B schematically illustrate cross sections of the PAP device of FIG. 6.
Figure 7B:
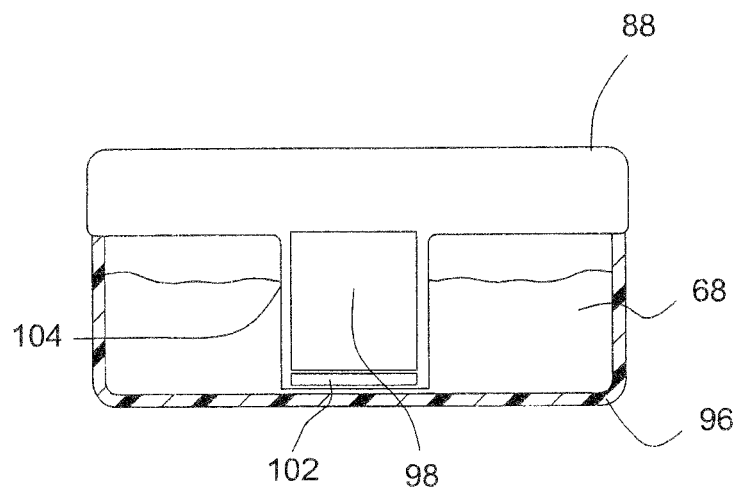
Figure 8:
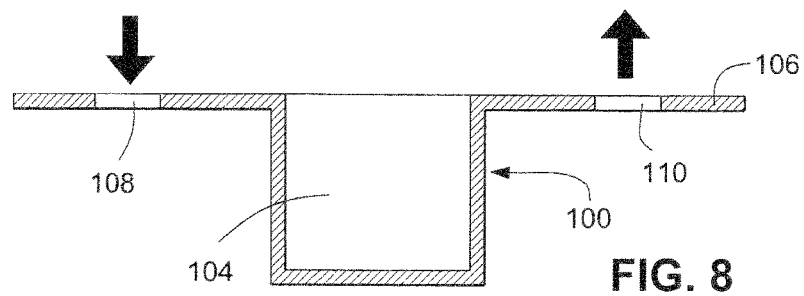
FIG. 8 schematically illustrates a blower motor assembly housing usable with the PAP device of FIGS. 6, 7A and 7B.

Referring to FIGS. 6-8, a PAP device 10 comprises a flow generator 86 and a humidifier 96. The flow generator 86 is configured to generate a flow of breathable gas, e.g. air, and includes a blower motor assembly 98 provided in a blower motor assembly housing 100. The blower motor assembly 98 may comprise at least one impeller that is rotatably driven by a motor. A blower motor assembly suitable for use in the embodiment shown in FIG. 6 is disclosed in, for example, WO 2007/134405 A1 and U.S. Patent Application Publication 2008/0304986 A1, the entire contents of both being incorporated herein by reference. The blower motor assembly 98 may be connected to an electrical connection 28, for example an electrical cord configured to be inserted into an AC outlet.

The blower motor assembly housing 100 may define a chamber 104 that is configured to house the blower motor 98 and a heater element 102, for example a heater plate. The chamber 104 may be formed of metal to improve heat conduction from the heater plate 102 to the water 68 in the humidifier 96. The metal of the chamber 104 may also improve heat conduction from the operation of the blower motor 98 to the water 68, which may reduce the amount of power that must be supplied to the heating plate 102. The temperature of the blower motor 98 may thus be regulated, which may increase bearing life. Reducing the power that must be supplied to the heating plate 102 may improve the efficiency in general, and also increase the scope for battery power of the flow generator 86 and the humidifier 96. Surrounding the blower motor assembly 100 with the humidifier and the water it contains act as sound insulation for radiated noise from the blower motor 98.

Referring again to FIG. 6, the flow generator 86 may comprise a flow generator housing 88 that is configured to be connected to the humidifier 96 in a substantially water tight manner. The housing 88 may be connected to the humidifier 96 by, for example, threaded engagement. A seal, or seals, 170 may be provided between the housing 88 of the flow generator 86 and the humidifier 96. The seal, or seals, between the housing 88 and the humidifier 96 may be provided above the maximum water fill level of the humidifier. As the humidifier may not include any seal or seals under the level of the water 68, the risk of leaks from the humidifier 96 is reduced.

The humidifier 96 may be formed, for example, from a single plastic mold and may contain no metal component for the purpose of heat conduction. The formation of the humidifier from plastic reduces the risk of corrosion.

The flow generator housing 88 comprises air inlets 95 formed in, for example, an outer peripheral surface. It should be appreciated that the air inlets may be formed at other locations on the flow generator housing 88. The flow generator housing 88 may include controls 92, such as buttons, and a display 94 configured to display, for example, operating parameters or settings of the PAP device 10. The housing 88 and humidifier 96 may be engaged by, for example, a threaded connection. A handle 90 may be provided to the housing 88 to permit the PAP device 10 to be carried or moved. Carrying or moving the PAP device 10 by the handle 90 may help ensure that the orientation of the PAP device 10 is correctly maintained and prevent spillage of the water 68 from the humidifier 96 into, for example, the blower motor assembly housing 100 or into a tube 128 connected to the humidifier 96 by a connector 126 at an outlet 124 of the humidifier 96. The humidifier 96 may also include a plurality of feet 144. The feet 144 may be made of, for example, rubber to increase the friction between the humidifier 96 and a supporting surface, such as a table adjacent the patient's bed, and to prevent sliding and/or tipping of the humidifier 96 on the support surface.

The PAP device 10 shown in FIGS. 6-7B requires fewer parts than currently available humidified PAP devices. The connection between the humidifier 96 and the flow generator 86 is also easier for patients than current PAP devices. The PAP device 10 is also less expensive than currently available humidified PAP devices. The tub of the humidifier 96 may be formed as one piece and be replaceable and/or washable. The humidifier 96 of the PAP device 10 may experience fewer leaks than currently available humidifiers and may not have any corrosion issues. The PAP device 10 may also be smaller than current PAP devices that include, or are usable with, humidifiers.

The tub of the humidifier 96 may be transparent. It should also be appreciated that the tub of the humidifier 96 may comprise a color. For example, a certain color may be assigned to indicate a particular device customization. The color may also serve as an indicator of a size, or volume, of the tub of the humidifier. Tubs intended to be used in colder regions may comprise insulation.

Referring to FIG. 8, the blower motor assembly housing 100 for the blower motor 98 may comprise a flange 106 having an inlet 108 and an outlet 110. The blower motor assembly housing 100 may be formed, for example, from a single piece forming the chamber 104 for the motor 98 and the bottom of the upper flower generator 86. Both the inlet 108 and the outlet 110 may be covered by flanges or other backspill prevention devices.

When the motor 98 of the blower motor assembly 100 is turned on, air is drawn in through the inlets 95 of the flow generator housing 88. The air moves in a circular fashion around the chamber 104 of the blower motor assembly housing 100 and over the water 68 and out through outlet 124, where it then passes into a hose, tube, or conduit 128 that is connected the outlet 124 by a connector 126. As shown in FIG. 6, the air inlets 95 are generally on an opposite side of the device 10 from the outlet 124 of the humidifier 96, although it should be appreciated that other arrangements are possible. It should also be appreciated that air inlets may be provided at more than one location in the device.

In a variant, the humidifying may be done on the atmospheric side of the turbine rather than the pressurized side. There are some advantages in doing so, including no need for pressure-tight humidifier seals, which has allows for easier separating of the humidifier from the flow generator, and no need to separate the circuit from humidifier. It also retains an entirely consistent interface to the user, in that the circuit connects only to the flow generator, which may improve styling issues. There is no pressure compensation required for the humidifier. Whatever flow channel is required for the humidification also acts as a flow channel for acoustics of the inlet. If closed-loop control of humidification is needed, the sensors can be built into the flow generator airpath rather than the circuit, with the associated sensor connection. The process of humidifier refilling without interrupting treatment is simplified, since there's no pressure gradient above atmosphere. The filter could be built into the flow generator with an air conduit down into the perimeter of the humidifier tub.

PAP Device Fourth Embodiment

Figure 9:
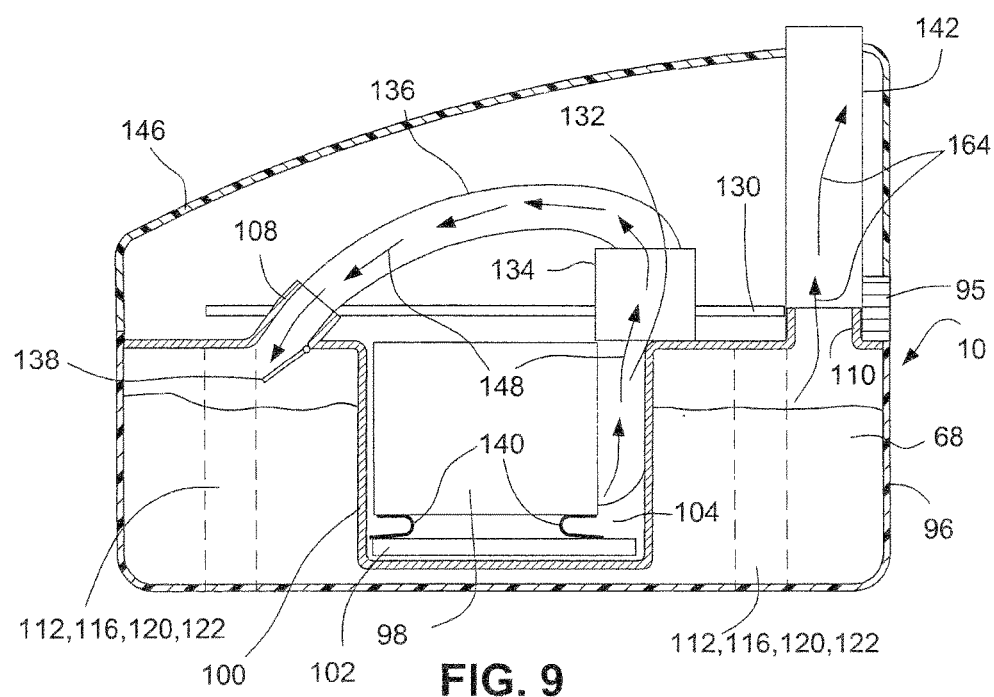
FIG. 9 schematically illustrates a PAP device including a humidifier according to another sample embodiment of the invention.

Referring to FIG. 9, a PAP device 10 according to another sample embodiments comprises a humidifier 96 configured to contain a supply of water 68. A blower assembly housing 100 is supported in the humidifier 96 and contains a chamber 104. A blower assembly 98 is provided in the chamber 104. Blower assemblies suitable for use are disclosed in, for example, WO 2007/134405 A1 and U.S. application Ser. No. 12/155,528, filed Jun. 5, 2008, the entire contents of each being incorporated herein by reference. A heater element 102, for example a heater plate, may also be provided in the chamber 104. The blower assembly 98 and the heater plate 102 may be connected by electrical connectors 104 to receive power from a common power source.

A lid 146 is provided to cover the humidifier 96 and the blower assembly housing 100. The lid 88 may be configured to present a low profile. As shown in FIG. 9, the chamber 104 of the blower assembly housing 100 is submerged in the water 68. The blower assembly housing 100 may be formed of, for example, metal to conduct heat from the heater plate 102, and the blower assembly 98, to the water 68. The water 68 may also absorb sound from the blower assembly 98 to reduce the noise of the operation of the device 10.

Ambient air is allowed to enter the PAP device 10 through inlets 95 formed in the lid 146. The blower assembly 98 creates a flow of air 148 that exits an outlet 132 of the chamber 104 of the blower assembly housing 100 and passes a flow sensor 134 into a hose, tube, or conduit 136 that extends to an inlet 108 of the blower assembly housing 100. The air flow 148 passes a flap 138 that may be pivotally connected to the housing 100 to cover the inlet 108. The air flow 148 then flows around the chamber 104 of the housing 100 and passes over the water 68 and is humidified. The humidified air flow 164 passes through an outlet 110 and into an outlet tube 142 that is connected to the outlet 110 of the housing 100. The humidified air flow 164 is conducted out of the device 10 through the outlet tube 142 which extends through the lid 146. The outlet tube 142 may be connected to a tube including heating element to provide heat to the humidified flow 164, for example to prevent condensation, or rain out, in the tube 142. Such a tube including a heating element is disclosed in, for example, U.S. Patent Application Publication 2008/0105257 A1, the entire contents of which are incorporated herein by reference. As the humidified flow passes back through the flow generator the connection of the heated tube does not require additional coupling to the humidifier.

The air flow 148 enters the humidifier 96 through the inlet 108 of the housing 100 and may pass through baffles. Baffle arrangements usable in the sample embodiment of FIG. 9 are shown in FIGS. 10A-10C.

Figures 10A, 10B, 10C:
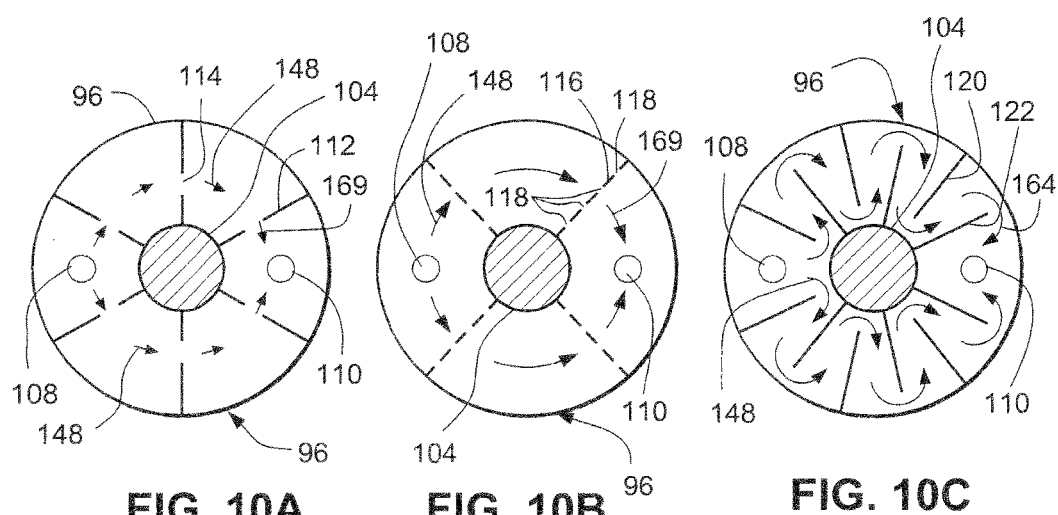
FIGS. 10A-10C schematically illustrate blower motor assembly housings usable with the PAP device of FIG. 9.

Referring to FIGS. 9 and 10A, the blower assembly housing 100 may comprise baffles 112 that each include an aperture 114. The air flow 148 enters the humidifier 96 through the inlet 108 and passes through the apertures 114 and passes over the water 68. The humidified air flow 168 then exits the humidifier 96 through the outlet 110 into the outlet tube 142.

Referring to FIG. 10B, in a variant embodiment, the blower assembly housing 100 may comprise baffles 116 that each include a plurality of apertures 118. In another variant embodiment shown in FIG. 10C, the blower assembly housing 100 may include alternating baffles 120, 122. Baffles 120 may extend radially inwardly from an outer edge of the blower assembly housing 100 and baffles 122 may extend radially outwardly from the perimeter of the chamber 104. The air flow 148 may assume a serpentine path from the inlet 108 to the outlet 122 as it passes the alternating baffles 120, 122.

The baffles 112; 116; 120, 122 reduce noise from the PAP device 10 that would otherwise be conducted down the air delivery tube. In the configuration shown in FIG. 10B, the baffles 116 have a grate-like composition. These baffles 116 may have the effect of further slowing air and reducing sound, compared to the configuration shown in FIG. 10A. The baffles 116 are also configured to keep the air flow 148 in contact with the water longer 68 and to reduce the noise of the PAP device 10.

In the configuration shown in FIG. 10C, the alternating baffles 120, 122 increase the length of the path that the air flow 148 must travel from the inlet 108 to the outlet 110. The baffles 120, 122 also reduce the amount of sound produced by the PAP device 10.

Referring again to FIG. 9, a controller 130 may be provided to control the supply of power to and operation of the blower assembly 98. The controller 130 may be, for example, a printed circuit board comprising a control circuit that receives signals from the flow sensor 134 and controls the blower assembly 98 and heater plate 102 to provide a humidified air flow 164 at predetermined humidity and/or temperature. Such a control circuit is disclosed in U.S. Patent Application Publication 2009/0223514 A1, the entire contents of which is incorporated herein by reference.

In order to prevent the water 68 in the humidifier 96 from backspilling into the chamber 104 and/or onto the controller 130, for example when the PAP device 10 is in transit and/or held at an angle unintended from a design standpoint, the flap 138 covers the inlet 108 of the blower assembly housing 100. The flap 138 may be biased into a position to cover the inlet 108 in the blower assembly housing 100. For example, the flap 138 may be connected to the housing 100 by a hinge and biased by a spring, such as a leaf spring or a coil spring. As another example, the flap 138 may be connected to the housing 100 by an integral, or living, hinge, that holds the flap 138 over the inlet 108 in a relaxed state. The pressure supplied to the air flow 148 by the blower assembly 98 should be at a level sufficient to provide a positive pressure difference across the flap 138 to overcome the bias and open the flap 138 and allow the air flow 148 to pass through the inlet 108 into the humidifier. The positive pressure difference that is sufficient to overcome the bias and open the flap 138 may be, for example, the lowest pressure generally prescribed for therapy. When blower assembly 98 is not operating, or is operating at a pressure below that necessary to open the flap 138, the flap 138 will close. This further precaution can be useful because people transporting the device may not be as conscious about the problems with water backspill if the device is not powered during transport.

PAP Device Components

Figure 11A:
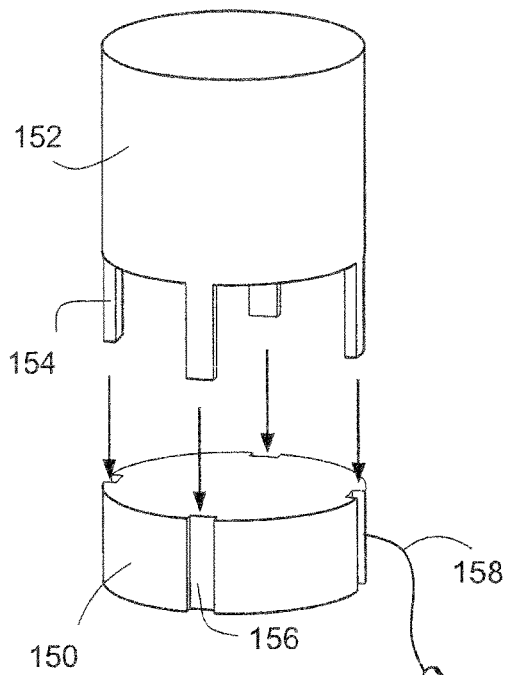
FIGS. 11A and 11B schematically illustrate a sample embodiment of a PAP device according to another sample embodiment of the invention.
Figure 11B:
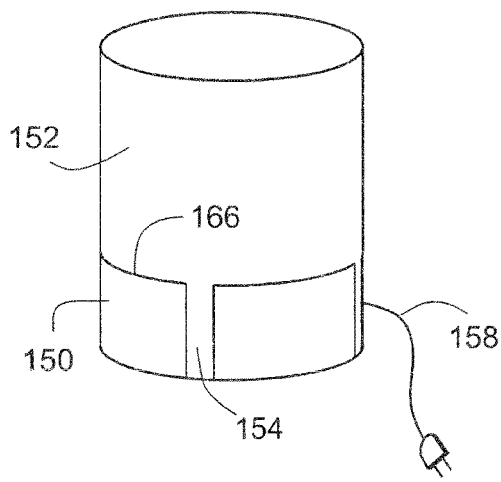

FIGS. 11A-12C illustrate further configurations for components of a PAP device that have provide structural integrity. Referring to FIG. 11A, an upper component 152 may be stacked on a lower component 150. The upper component 152, which may comprise, for example, a blower assembly, comprises tabs 154 that are insertable into slots 156 provided in the lower component 150. This configuration may prevent the components 150, 12 from being separated if the device is accidentally bumped into and/or knocked over. As shown in FIG. 11B, in the stacked, i.e. connected, configuration, the upper component 152 and the lower component 150 present a flush outer surface 166.

Power may be supplied to the device through an electrical connector 158. The tabs 154 and slots 150 may include complementary electrical connections so that power supplied to the lower component 150 is also provided to the upper component 152. It should also be appreciated that an electrical connector may be provided to the upper component instead of, or in addition to, the electrical connector 158.

Figure 12A:
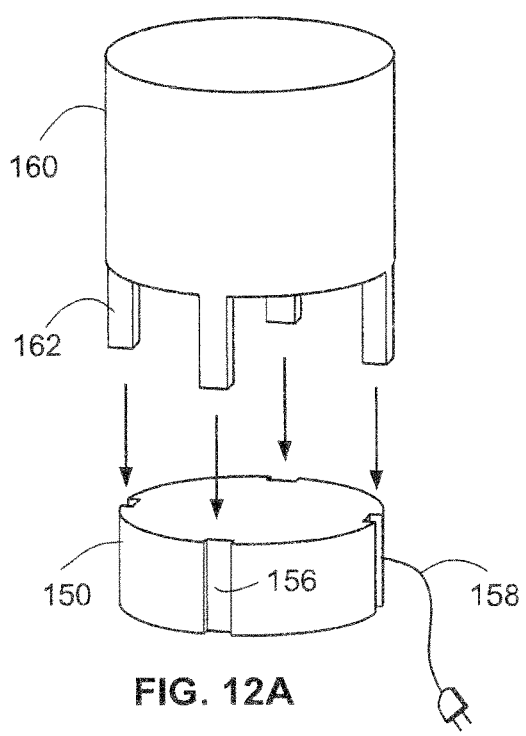
FIGS. 12A-12C schematically illustrate another sample embodiment of a PAP device according to the invention.
Figure 12B:
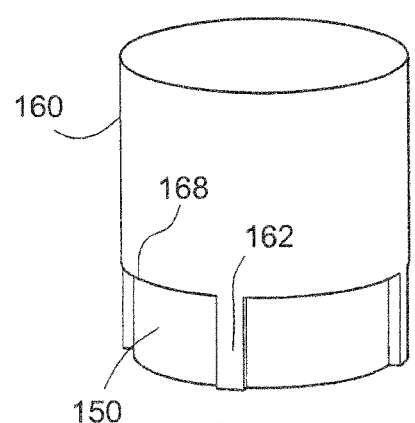
Figure 12C:
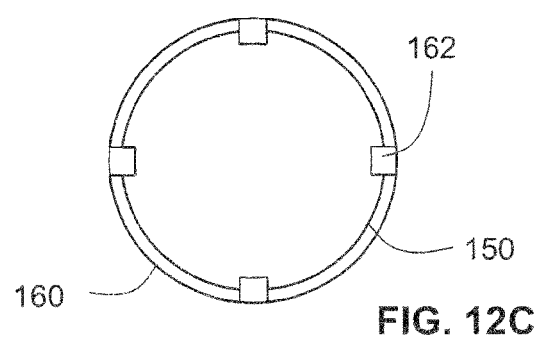

Referring to FIGS. 12A-12C, an upper component 160 may be connected to a lower component 150 by tabs 162 that are configured to be inserted into slots 156 provided in an outer surface of a lower component 150. As shown in FIG. 12B, when connected, an edge 168 of the upper component 160 extends beyond the outer surface of the lower component 150. Although this configuration, and other possible configurations, might slightly increase the footprint over that of the lower component (as shown in the bottom view of FIG. 12C), this configuration does not substantially increase the footprint of the PAP device.

The progressive reduction in size of turbines, electronics, and other components has resulted in flow generators and humidifiers of manageable size as disclosed in the instant application. In addition, circuit management, for example around the circularly symmetric power base, humidifier, and/or flow generator housing, offers options for circuit stowage (e.g. wrapping around).

Spill back protection is provided because the turbine is above the waterline. The closer the blower, or flow generator, outlet (into the humidifier) is to the center of the humidifier maximizes this advantage because tilting the system won't cause water ingress. Specific spill back protection may thus not be needed.

There is a consistent pneumatic impedance and acoustic path for both PAP devices, i.e. humidified and non-humidified. This means that adding a humidifier does not alter the pneaumtic capabilities of the device, and removes any need for the controller to be aware of the humidifier's presence.

A problem with prior designs is that an internal power supply unit, which has traditionally been considered more convenient for the user than external, and other power electronics are a source of heat within the flow generator housing as are the drive electronics for the motor. The flow generator housing is typically sealed for acoustic reasons, so that heat can be trapped. That trapped heat can contribute to bearing wear and surface temperatures. As described herein, the disclosed embodiments change this situation, in that by placing the power supply unit and the motor drive electronics in a separate compartment to the motor, (1) they separate the power supply unit and its heat from the turbine, (2) that heat is used to contribute to heating the water rather than being wasted, promoting efficiency, and (3) the power components are both separate but also in a defined configuration, so if cooling slots are found to be needed they can be in a controlled orientation.

In the embodiment shown in FIGS. 6-8, where the motor contributes to the heating of the water by immersion, the same concept is achieved by immersing (or conducting heat from) the power supply unit and motor drive electronics instead of the motor. This has different effects compared to the turbine immersion, but among the advantages is a greater heating capability, since the electronics can include the heater itself.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A positive airway pressure (PAP) device for supplying a flow of breathable gas to a patient, the PAP device comprising:
    housing;
    a flow generator secured within the housing and configured to pressurize a flow of breathable gas, the flow generator comprising a blower motor assembly; and
    a humidifier configured to be secured to the housing and receive and humidify the pressurized flow of breathable gas from the flow generator,
    wherein when the humidifier is secured to the housing, the flow generator and the humidifier are positioned so that heat originating from the blower motor assembly inside the housing is conveyed through the housing to water in the humidifier, and
    wherein the housing is configured to be directly exposed to the water in the humidifier.

2. A PAP device according to claim 1, wherein the flow generator comprises an internal power supply and the flow generator is configured to convey heat generated by the internal power supply to the water in the humidifier.

3. A PAP device according to claim 2, wherein the flow generator further comprises power supply electronics for controlling the internal power supply, and wherein the flow generator is configured to convey heat generated by the power supply electronics to the water in the humidifier.

4. A PAP device according to claim 1, wherein the flow generator comprises a blower with an impeller driven by the blower motor assembly, the blower being configured to pressurize the flow of breathable gas.

5. A PAP device according to claim 1, wherein the housing is configured to be submerged within the water in the humidifier.

6. A PAP device according to claim 4, wherein the flow generator further comprises motor drive electronics configured to control the blower motor assembly, and wherein the flow generator is configured to convey heat generated by the motor drive electronics to the water in the humidifier.

7. A PAP device according to claim 6, wherein the motor drive electronics are separated from the blower.

8. A positive airway pressure (PAP) device for supplying a flow of breathable gas to a patient, the PAP device comprising:
  housing;
  a flow generator secured within the housing and configured to pressurize a flow of breathable gas; and
  a humidifier configured to receive and humidify the pressurized flow of breathable gas from the flow generator, the humidifier comprising a tub configured to hold a volume of water,
  wherein a portion of the housing is configured to be immersed within the water in the tub and convey heat generated by the flow generator to the water in the humidifier when the flow generator is secured to the humidifier.

9. A PAP device according to claim 8, wherein the flow generator comprises a blower assembly, the blower assembly comprising an impeller and a motor configured to drive the impeller, the impeller being configured to pressurize the breathable gas.

10. A PAP device according to claim 9, wherein the motor is secured within the portion of the housing configured to be immersed within the water in the tub.

11. A PAP device according to claim 8, wherein the flow generator comprises an internal power supply, and wherein the internal power supply is secured within the portion of the housing configured to be immersed within the water in the tub.

12. A PAP device according to claim 8, wherein the flow generator comprises an internal power supply, a blower with an impeller, a blower motor assembly configured to drive the blower, and motor drive electronics configured to control the blower motor assembly.

13. A PAP device according to claim 12, wherein the internal power supply and the motor drive electronics are compartmentalized from the blower and are positioned within the housing so that heat generated by at least one of the internal power supply and the motor drive electronics is conveyed to the water in the tub when the flow generator is secured to the humidifier.

14. A positive airway pressure (PAP) device for supplying a flow of breathable gas to a patient, the PAP device comprising:
  a flow generator configured to pressurize a flow of breathable gas, the flow generator comprising a blower motor assembly;
  a power supply configured to provide power to the flow generator; and
  a humidifier positioned between the flow generator and the power supply, the humidifier being configured to receive and humidify the pressurized flow of breathable gas from the flow generator, the humidifier comprising a tub configured to hold a volume of water; and
  housing that contains the flow generator and the power supply,
  wherein the flow generator and the power supply are positioned relative to the humidifier so that heat originating from one or both of the blower motor assembly and the power supply is conveyed by conduction to the water in the tub when the tub contains water and the flow generator and the power supply are assembled to the humidifier, and
  wherein the housing is positioned to touch the water in the tub.

15. A PAP device according to claim 14, wherein a portion of the flow generator is configured to be positioned within the tub when the flow generator is secured to the humidifier.

16. A PAP device according to claim 15, wherein the flow generator comprises a blower with an impeller driven by the blower motor assembly, the blower being configured to pressurize the breathable gas.

17. A PAP device according to claim 16, wherein the blower motor assembly is positioned within the portion of the flow generator configured to be positioned within the humidifier when the flow generator is secured to the humidifier.

18. A PAP device according to claim 17, wherein the flow generator further comprises a heater configured to heat the water in the humidifier.

19. A PAP device according to claim 18, wherein the heater is positioned within the portion of the flow generator configured to be positioned within the humidifier when the flow generator is secured to the humidifier.

20. A PAP device according to claim 14, wherein a portion of the power supply is configured to be positioned within the humidifier when the power supply is secured to the humidifier.

21. A PAP device according to claim 14 further comprising housing that contains the flow generator and the power supply, wherein the housing is positioned to be submerged within the water in the tub.

* * * * *